United States Patent [19]

Chen et al.

[11] Patent Number: 5,118,192
[45] Date of Patent: Jun. 2, 1992

[54] SYSTEM FOR 3-D INSPECTION OF OBJECTS

[75] Inventors: Sullivan Chen, Centerport; William E. Yonescu, Dix Hills; Howard K. Stern, Greenlawn, all of N.Y.

[73] Assignee: Robotic Vision Systems, Inc., East Hauppauge, N.Y.

[21] Appl. No.: 551,150

[22] Filed: Jul. 11, 1990

[51] Int. Cl.$^5$ .............................................. G01B 11/24
[52] U.S. Cl. ..................................... 356/376; 356/372
[58] Field of Search ............................ 356/375–376, 356/237, 377, 378–381, 445–448; 250/560–561

[56] References Cited

U.S. PATENT DOCUMENTS

| | | | |
|---|---|---|---|
| 4,097,160 | 6/1978 | Yataki et al. | 356/446 |
| 4,286,852 | 9/1981 | Stern et al. | 356/376 |
| 4,529,316 | 7/1985 | DiMatteo | 356/376 |
| 4,553,844 | 11/1985 | Nakagawa et al. | 356/376 |
| 4,583,857 | 4/1986 | Grammerstorff et al. | 356/375 |
| 4,888,490 | 12/1989 | Bass et al. | 250/561 |

FOREIGN PATENT DOCUMENTS

| | | | |
|---|---|---|---|
| 0190607 | 10/1984 | Japan | 356/376 |
| 0043507 | 8/1985 | Japan | 356/376 |
| 0029710 | 2/1986 | Japan | 356/376 |

OTHER PUBLICATIONS

SPIE, Robotic Vision (1982) pp. 121–127, "Automatic Visual Inspection of Solder Joints on Printed Circuit Board".

Primary Examiner—Richard A. Rosenberger
Assistant Examiner—Hoa Pham
Attorney, Agent, or Firm—Robin, Blecker, Daley & Driscoll

[57] ABSTRACT

An inspection system for irregular objects such as solder joints wherein the system utilizes first and second sensors adapted to be pivotable about a common pivot axis and such that the projection axes of the sensors and the pivot axes are able to intersect at a common.

30 Claims, 4 Drawing Sheets

SYSTEM FOR 3-D INSPECTION OF OBJECTS

BACKGROUND OF THE INVENTION

This invention relates to an apparatus and method for the inspection of objects and, in particular, to an apparatus and method for automatic three-dimensional (3-D) inspection of such objects.

In many applications today, the inspection of objects or assembled parts is carried out manually. However, manual inspection is often inconsistent due to a variety of factors which tend to impair the ability of the human inspector. These factors include tiredness, ill health or distractions caused by mental state, surroundings or otherwise. Also, manual inspection is costly and tedious.

Because of these disadvantages, attention has been directed toward automating the inspection process. Unfortunately, inspection of objects requires the exercise of a great deal of judgment and the ability to view an object from many angles. These requirements make the process complex and have impeded the development of automatic inspection systems, especially for applications where manual inspection is satisfactory.

The prior art inspection systems developed to date have extensively used two-dimensional (2-D) machine vision or sensors and have proved successful in certain applications. These sensor systems have also incorporated mechanisms for measuring the reflectance of the object to gather additional data for making decisions. This is accomplished by measuring the brightness of the reflected light to form a gray-scale which can be used to define part boundaries. Pixels, unit areas within the sensor field of view, are counted for each gray scale level found and the results fit to a template of acceptable parts or objects to provide a basis for a statistical decision.

X-rays have also been used for inspecting objects and, in particular, for inspecting solder joints or connections. These x-ray systems use techniques similar to the 2-D techniques discussed previously. Also, solder joint inspection has been carried out using laser pulse heating in conjunction with a thermal imaging infrared sensor. In this case, the heating and cooling profile are compared with that of a known solder joint in order to decide if the joint is acceptable.

Solder joint inspection is an example of a broad class of objects and parts for which the inspection problem is compounded due to the irregular contoured features of these parts. Such irregularities make it difficult to define the inspection procedure and acceptance criteria. In particular, since a solder joint is not a machined part, no template is precisely specified that can be used for its inspection.

Accordingly, single feature determination is not adequate for inspection of solder joints and other like irregular parts. Many features must be considered and the features must be considered in associated combinations. Basic to these considerations is the ability to accurately measure the features so that pass/fail determinations can be made. By measuring the 3-D rather than 2-D characteristics of the features, a great deal of the ambiguity can be removed from the inspection process. U.S. Pat. No. 4,553,844 is an example of a system which uses 3-D analysis and triangulation techniques for solder joint inspection. The '844 patent points out that in systems of this type, where optical triangulation is used to make 3-D measurements, mirror-like surfaces produce specular reflections that increase the difficulty of measurement by producing false images.

Another discussion of the application of structured light to produce 3-D measurements for inspection can be found in SPIE, Volume 336, Robot Vision (1982) page 121 through 127 entitled, "Automatic Visual Inspection of Solder Joints on Printed Circuit Boards". Various common defects are described which the inspection system must detect since such defects normally are not revealed by electrical test.

It is an object of the present invention to provide an improved apparatus and method for the inspection of assembled parts or objects and, in particular, the inspection of solder joints.

SUMMARY OF THE INVENTION

In accordance with the principles of the present invention, the above and other objectives are realized in an apparatus and method in which first and second sensor means having first and second projection axes, respectively, are provided. The first and second sensor means are further adapted to be pivotable about a first common axis which is intersected by the first and second projection axes at substantially a common point or region.

The first and second sensor means also have first and second collection or viewing axes, respectively, which define with the first and second projection axes, first and second sensor measurement planes. The sensors are further adapted such that the first and second viewing directions also intersect at the common point or region and, preferably, such that the first common axis lies in the first and second measurement planes.

In the embodiment of the invention to be disclosed, hereinafter, the first and second sensor means are independently pivotable about the first common pivot axis. Additionally, the first and second sensor means are further adapted to be commonly pivotable about a second common pivot axis traverse to the first common axis.

In this embodiment also, a support surface is further provided for supporting the object to be inspected and the support surface and the first and second sensor means are translatable relative to each other in at least a first translation direction and, preferably, first, second and third mutually orthogonal translation directions. In the embodiment, the first and second sensors are translatable in the first translation direction and the support surface translatable in the second and third translation directions. Finally, in this embodiment, cameras and a display monitor allow broad and zoom viewing of the object on the object surface so as to aid in adjustment of the pivoting and translation means.

BRIEF DESCRIPTION OF THE DRAWINGS

The above and other features and aspects of the present invention will become more apparent upon reading the following detailed description in conjunction with the accompanying drawings, in which.

DESCRIPTION OF THE PREFERRED EMBODIMENT

Figure 1:
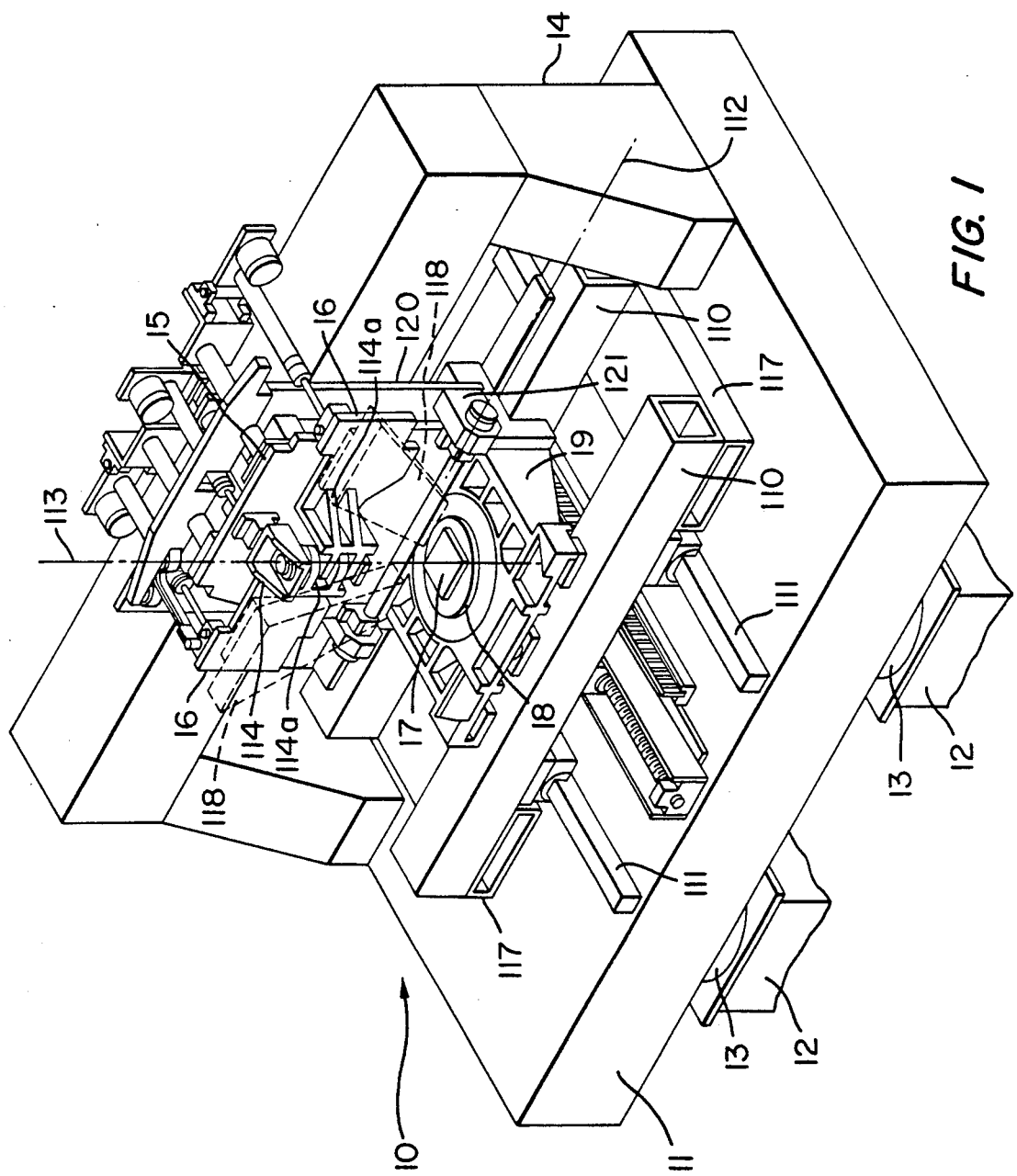
FIG. 1 shows an overall view of the mechanical assembly of a system in accordance with the principles of the present invention for use in inspecting circuit board solder joints.

FIG. 1 shows an overall view of an assembly 10 forming the mechanical part of an inspection system in accordance with the principles of the present invention. The inspection system is designed for solder joint inspection and the assembly 10 includes a dimensionally stable platform 11 which is supported by legs 12. Preferably, the legs 12 include at the interface with the platform 11 means 13 for isolating the platform from any shock and vibration imparted to the legs 12 by the floor upon which assembly 10 is mounted.

Figure 3B:
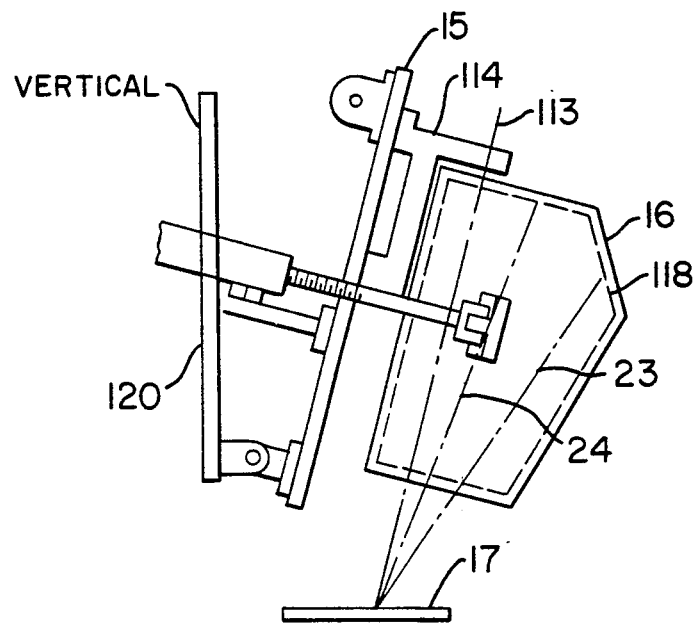
FIG. 3b shows a side view of the "butterfly" sensor assembly with the sensor "wings" partially rotated.
Figure 3A:
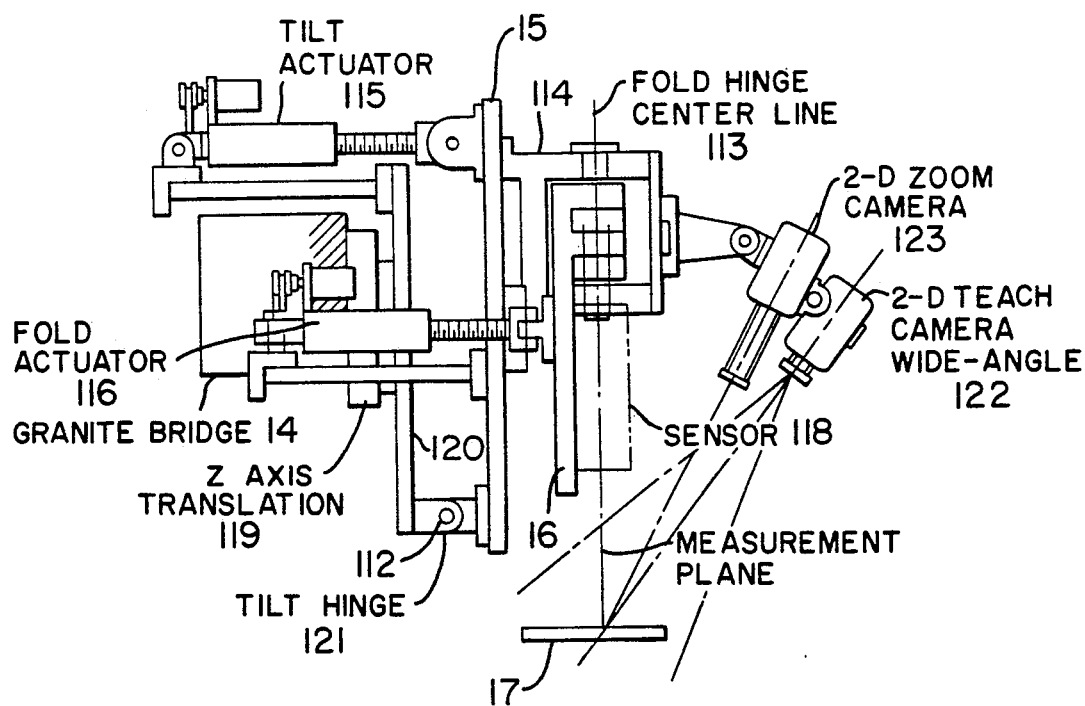

A dimensionally stable bridge 14 made of granite is mounted stationarily upon platform 11 which provides support for vertical rails 119 (shown in FIG. 3a but not visible in FIG. 1). The latter rails hold a movable base 120 and provide directional guideways for translation of base vertically. A hinge 121 mounted on base 120 provides support for a plate 15 and enables the plate to be pivoted about an axis 112. Two further plates 16 are mounted upon plate 15 via hinge arms 114a of a further hinge 114 having a pivot or rotation axis 113. In the case shown, the hinge arms 114a are formed integrally with the respective plates 16, although the hinge arms and the plates can also be separate elements which are affixed to one another.

Actuator 115 (FIGS. 2 and 3) enables control forces to be applied to plate 15 so as to pivot it about axis 112, while actuators 116 enable similar control forces to be applied to plates 16 to pivot them about axis 113.

Plates 16 provide a base upon which 3-D optical triangulation sensors 118 are mounted for inspecting the solder joints on a circuit board 17. Sensors 118 can, therefore, be rotated or pivoted about the common axis of rotation 113 via pivoting of the plates 16 through hinge 114. These plates and sensors, together with the hinge 114, resemble a butterfly and are referred to hereinafter as the "butterfly" sensor assembly.

Circuit board 17 is mounted upon a rotary table 18 which is mounted, in turn, upon a translation table 19. The circuit board 17 may be carried by a standard pallet. If a pallet of ferrous material is used, the pallet may be readily secured to the table 18 via a magnetic clamp. If a pallet of non-ferrous material is used mechanical grippers can be employed to couple the pallet to the table.

Rails 110 support translation table 19 and provide directional guideways for translation of the table 19 and, therefore, the table 18 in a first horizontal direction. Rails 110 are tied together via cross beams 117 to form an open frame which is supported by rails 111 that provide directional guideways for translation of table 19 and with it the table 18 in a second horizontal direction orthogonal to the first.

Translation of table 18 via table 19 along the directions of rails 110 and 111 enable the sensors 118 to view all portions of board 17. Sensors 118, which will described in greater detail below, acquire a swath of 3-D surface point measurements of a solder joint as board 17 is translated along rails 110. Since data is acquired while moving along rails 110, it is desirable that any deviations from an ideal straight path be reduced to values small compared to the desired measurement accuracy which, typically, might be of the order of 125 micro inches. Accordingly, air bearings are preferably used for translating the table 19 along the rails 110 to achieve the desired level of performance. Air bearings also reduce wear, friction and the required energy to drive the table. This results in longer life for the assembly 10.

Also, to assure smooth scanning along rails 110 a linear induction motor is preferably employed to drive table 19 therealong. Such a motor provides the lowest inertia for a low profile drive.

Rotation of table 18 is not performed during data acquisition. Therefore, this rotation can be imparted using a belt drive with a stepper motor. Likewise, since data is not acquired while translating table 19 along rails 111, the rails 111 may be standard quality TDK rails with a ball screw drive turned by a stepper motor. All movable parts of the assembly 10 should have any freeplay removed to eliminate any error contribution from that source.

Figure 2A:
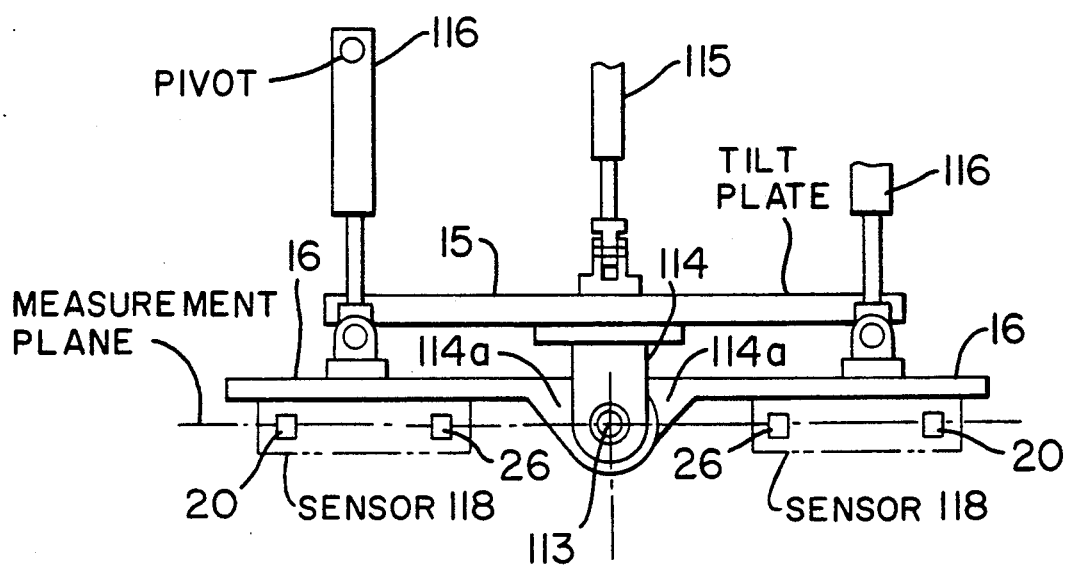
FIGS. 2a, 2b and 3a show a top, front and side views of the "butterfly" sensor assembly of the system of FIG. 1.
Figure 2B:
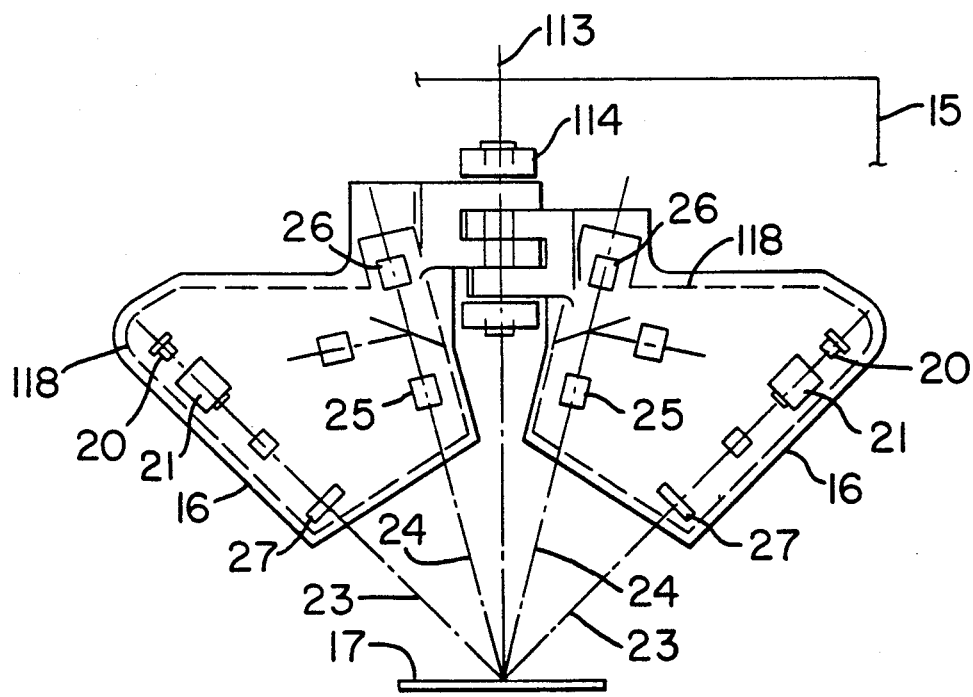

FIGS. 2a, 2b and 3a show the plates 16 and sensors 118 and their respective mounting components of assembly 10 in greater detail. As shown, the sensors 118 are mounted on the front side of their respective plates 16, although if more convenient, mounting on the back side is also possible. As can be best seen in the top view of FIG. 2a, plates 16 are each supported by arms 114a of hinge 114 so as to permit independent pivoting or rotating about axis 113 relative to plate 15 to which hinge 114 is attached.

As shown in FIG. 2b, each sensor 118 comprises like components. More particularly, each sensor 118 comprises a source of electromagnetic radiation or light 20 (not necessarily limited to the visible spectrum) which typically might be a solid state laser diode. Source 20 projects a narrow light beam along projection axis 23 toward the board 17. The light beam passes through a beam deflector 21 and a lens 27 before reaching the board.

The deflector 21 may be an acousto-optic, galvanometer driven mirror, holographic or other type deflector and controllably deflects the beam to broaden the measurement coverage to more than one position on the board 17. Rapid deflection, produces a swath of data as board 17 is transported beneath the deflected beam.

Light reflected from solder joints on board 17 in the direction of lens 25 is collected along a collection or viewing axis 24. The collected light is imaged by lens 25 upon a photosensitive surface of a detector 26. Projection axis 23 and view axis 24 form a plane that is defined as the measurement plane for the respective sensor 118. Detector 26 of each sensor 118 is aligned to lie in this plane.

Because projection axis 23 and view axis 24 intersect at an angle, the position of the image of the solder joint surface point or region along the length of detector 26 is proportional to the distance of the surface point or region from sensor 118. Thus, the depth dimension of the point or region can be measured from the data obtained from each sensor 118. Determination of the surface point or region dimensions orthogonal to the depth dimension can, in turn, be derived from the known position of the board 17 and the deflection angle of projection direction 23 transverse to the plate 16.

To allow plates 16 and, therefore, sensors 118, to pivot about axis 113 to obtain more favorable measurement angles without causing the common view areas of the two sensors 118 to separate, the center of the sensor view volumes and, thus, the view axes of the sensors as well as the projection axes of the sensors intersect the pivot axis 113 at a common point or region. As the plates 16 pivot, the segments of the projected beams within the field of view of the respective detectors 26 thus pivot about axis 113 keeping the data from the two sensors 118 closely located at all times.

The sensors 118 are additionally adapted to comply with the practice in copending application U.S. Ser. No. 445,121, the teachings of which are incorporated herein by reference, to provide data in a form that reduces the amount of computation necessary to produce inspection results. Thus, by requiring that the projection axes 23 of the sensors 118 intersect on axis 113 at a common point for all angles of rotation of plates 16, the axes remain coplanar as dictated by the practice of the '121 application. Further by always rotating plates 16 equal and opposite angles from the direction of travel of board 17 along rails 110, it is assured that the coplanar planes defined by the projection axes are parallel to the board 17 translation direction. This assures that the data being sensed by the two sensors is coplanar as is illustrated in FIG. 3b. Furthermore, due to the symmetric configuration of the sensors, both projection axes 23 may be deflected by equal amounts by their respective deflection means 21 and still remain coplanar.

A time penalty is paid if data for each solder joint surface point on board 17 is acquired sequentially from the two sensors 118. This time penalty may be avoided by using projected light or electromagnetic energy of different wavelengths for the two sensors. Simultaneous projection may then be used and bandpass filters, tuned to their respective sensor's wavelength, interposed along view axes 24 to allow the correct wavelength to reach the detector 26.

As can be appreciated, the two sensors 118, mounted to have different view axes, overcome the problems of surface obscuration and specular reflection. Also, since the sensors 118 may also pivot about axis 113, greater flexibility in avoiding obscuration and specular reflections is possible. This flexibility can be further enhanced by adapting the sensors 118 to pivot about axis 113 over an angle greater than the approximate 90° angle of rotation shown in the present illustrative case.

The ability to tilt the plate 15 about axis 112 is illustrated in FIGS. 3a and 3b. While, in the case shown, the plate 15 can only pivot through an angle of approximately 90°, it is within the contemplation of the invention that the plate 15 can be modified to pivot through greater angles. The purpose of pivoting the plate 15 is again to avoid obscuration and specular reflections.

Vertical translation of base 120 along rails 119 is provided by a stepper motor driven ball screw. The vertical travel enables centering of the common intersection point of the projection and view axes and the pivot axis 113 and, therefore, the center of view of sensors 118, on surfaces of various heights on board 17 for all tilt angles of plate 15. No data is acquired while translating along rails 119 or pivoting about axes 112 and 113. Therefore, motion precision is not essential, but repeatability is. All free-play in these motions must be removed to eliminate errors from these sources.

Figure 4:
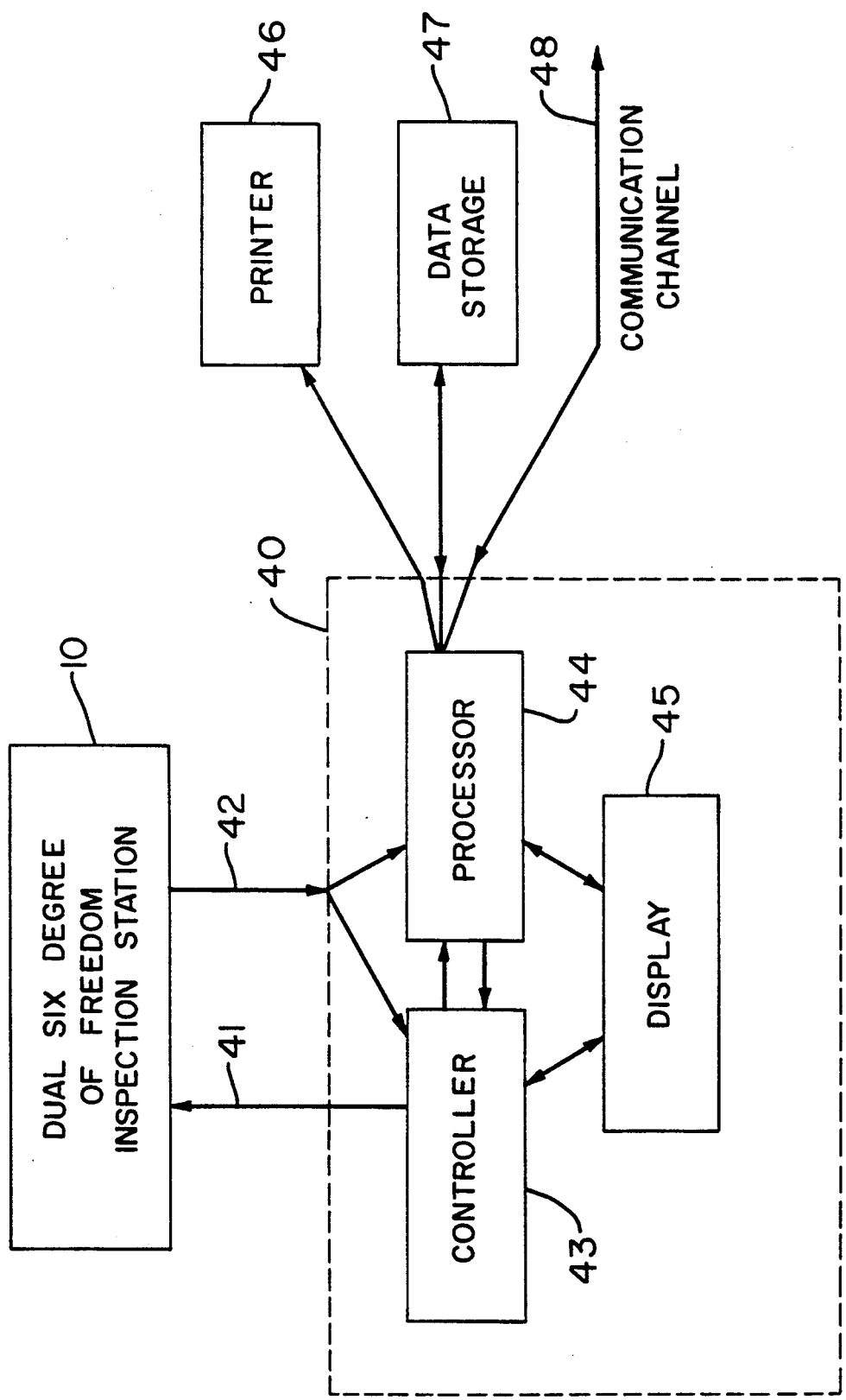
FIG. 4 illustrates a block diagram of the control section of the inspection system of the invention.

FIG. 4 shows a block diagram of the portions of the inspection system which provide control over the assembly 10 and analysis of the desired data. More particularly, as can be appreciated from the above, the components of the assembly 10 taken together are capable of providing three linear motions, one rotary motion and three pivotable motions (providing six degrees of freedom) in effecting the relative position between the sensors 118 and the table 18 carrying the board 17 being inspected. A processor/controller display unit 40 provides the control signals 41 to effect the necessary control of the assembly 10 components.

In particular, in a training phase of the system, an operator leads the system through the desired inspection paths with the assistance of an overhead 2-D camera 122 (shown only in FIG. 3a for clarity) mounted on plate 15 and which facilitates coarse positioning of board 17. The projected light beams of the sensors 118 along axes 23 are visible to camera 122 at the point where they reflect from the board 17. A second 2-D camera 123 (again, shown only in FIG. 3a for clarity) mounted on the camera 122 provides a zoomable view of the inspection view volume and enables the operator to fine position the sensors 118. Since the two projection axes 23 and the light beams of the sensors 118 intersect in the center of the view volume, the operator can raise or lower the sensors 118 along rails 119 until the two reflecting spots merge into one. The operator then pivots the sensors 118 about axes 113 and 112 for the best angles to take measurements. The path positions selected by the operator are then stored in the memory of the controller 43 for automatic path scanning. The display from each camera may be viewed singularly or combinedly on a single TV monitor with 3-D contours.

Since the pivoting axis 112 may be offset from the center of the view volume, i.e., the common intersection point of the axes 23 and the axis 113, as shown in FIG. 3a, pivoting the sensors 118 about axis 112 may cause the area of interest on the board 17 to move out of the view volume. Accordingly, the control algorithms of the controller 43 should be adapted to drive the vertical and horizontal translation motors of the assembly 10 in a manner to maintain the center of the view volume stationary with respect to the area of interest as plate 15 pivots.

Signals 42 from machine 10 comprise of video signals from sensors 118 and encoder signals developed for axes that do not have sufficient positioning accuracy. Controller 43 provides processor 44 with instantaneous position information while data is being acquired. Processor 44 combines this information and data with the relative 3-D measurements derived from the sensor 118 video signals to form the absolute 3-D measurements of the inspected surface. The measured data are preferably indicative of contours that are readily compared to contours obtained on reference parts. Processor 44 then analyzes the data and passes the results to display 45 and other operator selected destinations such as a printer 46, data storage device 47 and/or communication channel 48. Communication channel 48 and processor 44 may have the capability of accepting standard CAD/CAM data describing joint types and locations. This may reduce the effort required to train the system for particular boards.

Display 45 is also used during the training of the system to provide prompts to the operator and allow the operator to enter factual data such as the part number, type of solder joint or preferred analysis method. Display 45 is also capable of displaying, in various textual and graphical formats, the measured data for operator evaluation.

Display 45 provides the operator interface to initiate fully automatic inspection of a trained system and supplies monitoring information and error messages while the inspection is in progress. The operator is provided with a means of interrupting and restarting the inspection at any point.

It should be noted that while it is preferable to utilize two sensors 118 and associated plates 16 and hinge arms 114a, 114b in the assembly 10, it is within the contemplation of the invention to use only a single sensor, plate and hinge arm combination mounted to the hinge 114. In such case, the single sensor combination would be pivotable so as to be able to take measurements from the positions of both the sensor combinations of the illustrated system 10. The single sensor combination would thus be operated to take a first set of measurements with the sensor combination positioned to take measurements normally taken by the first sensor combination of the illustrated system and then a second set of measurements with the sensor combination positioned to take measurements which would normally be taken by the second sensor combination of the illustrated system.

In all cases, it is understood that the above-identified arrangements ar merely illustrative of the many possible specific embodiments which represent applications of the present invention. Numerous and varied other arrangements can readily be devised in accordance with the principles of the present invention without departing from the spirit and scope of the invention.

What is claimed is:

1. An apparatus for inspecting objects comprising:
   first sensor means for projecting electromagnetic radiation along a first projection axis and viewing reflected radiation along a first viewing axis;
   second sensor means for projecting electromagnetic radiation along a second projection axis and viewing reflected radiation along a second viewing axis;
   said first and second sensor means being adapted to be independently pivotable about a first common pivot axis and being further adapted such that said first and second projection axes and said first and second viewing axes intersect said first common pivot axis at substantially a common point.

2. An apparatus in accordance with claim 1 further comprising:
   a support means having a support surface for supporting said object;
   and means for effecting relative translation in a least one direction between said support surface and both said first and second sensor means.

3. An apparatus in accordance with claim 2 wherein: said means for effecting relative translation effects same in three mutually orthogonal directions.

4. An apparatus in accordance with claim 3 wherein: said means for effecting includes: means for commonly translating said first and second sensor means along a first direction; and means for translating said support surface in second and third directions orthogonal to said first direction.

5. An apparatus in accordance with claim 4 wherein: said first direction is vertical and said second and third directions are each horizontal.

6. An apparatus in accordance with claim 2 wherein: said first and second sensor means are commonly pivotable about a second common pivot axis orthogonal to said first common pivot axis.

7. An apparatus in accordance with claim 2 further comprising:
   means responsive to said first and second sensor means and to said means for effecting relative translation for controlling same and for developing data as to the 3-D location of points on the surface of said object.

8. An apparatus in accordance with claim 2 further comprising:
   camera means for viewing said object on said support surface.

9. An apparatus in accordance with claim 8 wherein: said camera means includes means for zooming in on areas of said object surface.

10. An apparatus in accordance with claim 2 wherein:
    each said first and second sensor means comprises: a sensor; and a support plate to which said sensor is affixed;
    and said first and second sensor means together comprise: a common hinge means having first, and second hinge arms which pivot about said first common pivot axis and to which are affixed the support plates of said first and second sensors, respectively; said hinge means being supported by said support means above said support surface.

11. An apparatus in accordance with claim 10 wherein:
    said hinge means is supported on said support means to be translatable relative to said support surface.

12. An apparatus in accordance with claim 11 wherein:
    said hinge means is further supported on said support means to also be pivotable about a second common pivot axis.

13. An apparatus in accordance with claim 12 wherein:
    said support means comprises actuator means for controlling and adjusting the pivoting of said first and second arms and of said hinge means.

14. An apparatus in accordance with claim 11 wherein:
    said support means comprises: first and second rails to which is mounted said support surface so as to be translatable in a first direction;
    and third and fourth rails to which are mounted said first and second rails so as to be translatable in a second direction orthogonal to said first direction.

15. An apparatus in accordance with claim 14 wherein:
    said support means further comprises: air bearings for translatable mounting said first and second rails to said third and fourth rails.

16. An apparatus in accordance with claim 2 wherein: said means for effecting relative translation includes linear adjusting means for linearly controlling said translation.

17. A method for use in inspecting objects comprising:
    projecting electromagnetic radiation along a first projection axis and viewing reflected radiation along a first viewing axis with a first sensor means;
    projecting electromagnetic radiation along a second projection axis and viewing reflected radiation along a second viewing axis with a second sensor means;
    independently pivoting said first and second sensor means about a first common pivot axis;
    and said first and second projection axes and said first and second viewing axes intersecting with said first common pivot axis at substantially a common point.

18. A method in accordance with claim 17 further comprising:

supporting said object on a support means having a support surface;

and effecting relative translation in a least one direction between said support surface and both said first and second sensor means.

19. A method in accordance with claim 18 wherein: said relative translation is effected in three mutually orthogonal directions.

20. A method in accordance with claim 19 wherein: said step of effecting relative translation includes: commonly translating said first and second sensor means along a first direction; and translating said support surface in second and third directions orthogonal to said first direction.

21. A method in accordance with claim 20 wherein: said first direction is vertical and said second and third directions are each horizontal.

22. A method in accordance with claim 18 further comprising:
commonly pivoting said first and second sensor means about a second common pivot axis orthogonal to said first common pivot axis.

23. A method in accordance with claim 18 further comprising:
developing data from said first and second sensors as to the 3-D location of points on the surface of said object.

24. A method in accordance with claim 18 further comprising:
viewing said object on said support surface.

25. A method in accordance with claim 24 wherein: said viewing step includes zooming in on areas of said object surface.

26. A method in accordance with claim 18 wherein: said step of independently pivoting said sensors comprises: pivoting first and second hinge arms of a pivot means to which are affixed support plates supporting said first and second sensors, respectively; said hinge means being supported above said support surface.

27. A method in accordance with claim 26 wherein: said step of effecting relative translation includes: translatable said hinge means relative to said support surface.

28. A method in accordance with claim 27 further comprising:
pivoting said hinge means about a second common pivot axis.

29. A method in accordance with claim 28 further comprising:
controlling and adjusting the pivoting of said first and second arms of said hinge means.

30. A method in accordance with claim 27 wherein: said step of effecting relative translation includes: translating said support surface in a first direction on said first and second rails; and translating said first and second rails in a second direction orthogonal to said first direction on third and fourth rails.

* * * * *